United States Patent [19]

Bastian

[11] 4,144,337
[45] Mar. 13, 1979

[54] 1,4-SUBSTITUTED PIPERAZINYL DERIVATIVES USEFUL AS PSYCHOSTIMULANTS

[75] Inventor: Jean-Michel Bastian, Therwil, Switzerland

[73] Assignee: Sandoz Ltd., Basel, Switzerland

[21] Appl. No.: 768,513

[22] Filed: Feb. 14, 1977

[30] Foreign Application Priority Data

Feb. 17, 1976 [CH] Switzerland .................. 1903/76
Feb. 17, 1976 [CH] Switzerland .................. 1905/76
Feb. 17, 1976 [CH] Switzerland .................. 1906/76
Feb. 17, 1976 [CH] Switzerland .................. 1907/76

[51] Int. Cl.² ............................................. A01N 9/00
[52] U.S. Cl. .................................. 424/250; 542/405; 542/429; 542/431; 542/432; 542/468; 542/440; 542/474; 542/470; 424/275; 424/278
[58] Field of Search ............... 542/440, 470, 405, 429, 542/431, 432, 468, 474; 424/250

[56] References Cited

U.S. PATENT DOCUMENTS

| | | | |
|---|---|---|---|
| 2,882,271 | 4/1959 | Janssen | 542/440 |
| 3,459,745 | 8/1969 | Fouche | 542/470 |
| 3,480,624 | 11/1969 | Fouche | 542/470 |
| 3,511,841 | 5/1970 | Archer | 542/470 X |
| 3,719,679 | 3/1973 | Boissier | 542/470 X |

*Primary Examiner*—Paul F. Shaver
*Attorney, Agent, or Firm*—Gerald D. Sharkin; Robert S. Honor; Thomas O. McGovern

[57] ABSTRACT

The invention provides compounds of formula I,

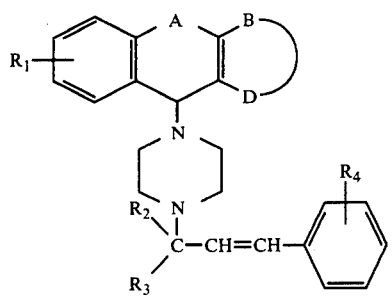

wherein each of $R_1$ and $R_4$, which may be the same or different, is hydrogen, halogen, alkyl or alkoxy; each of $R_2$ and $R_3$ is hydrogen, or together, oxygen; B and D together with the carbon atoms to which they are bound may be a benzene ring or a substituted or unsubstituted thiophene ring and A may, for example, be oxygen, sulpur, —CH₂—O—, —CH₂—S, ethylene or vinylene, useful as psychostimulants and vigilance-increasing agents.

14 Claims, No Drawings

1,4-SUBSTITUTED PIPERAZINYL DERIVATIVES USEFUL AS PSYCHOSTIMULANTS

The present invention relates to 1,4-substituted piperazinyl derivatives.

More particularly, the present invention provides compounds of formula I,

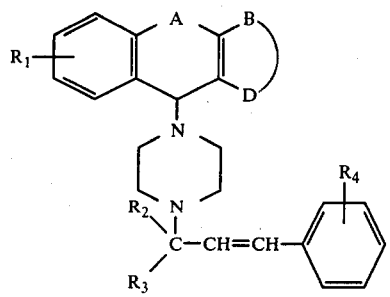

wherein each of $R_1$ and $R_4$, which may be the same or different, is hydrogen, halogen of atomic number from 9 to 35, alkyl of 1 to 4 carbon atoms or alkoxy of 1 to 4 carbon atoms, either each of $R_2$ and $R_3$ is hydrogen or $R_{2\ [4,5]}$ and $R_3$ together are oxygen, either B and D together with the carbon atoms to which they are bound form a benzene ring, or B is sulphur and B and D together with the carbon atoms to which they are bound form a thiophene ring which may be substituted in the position α- to the sulphur atom with halogen of atomic number from 9 to 35 or alkyl of 1 to 4 carbon atoms, and when B and D together with the carbon atoms to which they are bound form a benzene ring, A is oxygen, sulphur, —CH$_2$—O— or —CH$_2$—S— in either orientation, or a group of formula

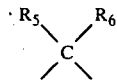

wherein each of $R_5$ and $R_6$, which may be the same or different, is alkyl of 1 to 4 carbon atoms, or when B is sulphur and B and D together with the carbon atoms to which they are bound form a substituted or unsubstituted thiophene ring, A is a group of formula

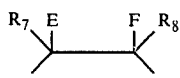

wherein each of $R_7$ and $R_8$, which may be the same or different, is hydrogen or alkyl of 1 to 4 carbon atoms and either each of E and F is hydrogen or E and F together form a bond.

When $R_1$ is alkyl or alkoxy, this is preferably alkyl of 1 or 2 carbon atoms or alkoxy of 1 or 2 carbon atoms, especially methyl or methoxy. When $R_1$ is halogen, this is preferably chlorine. When B and D together with the carbon atoms to which they are bound form a benzene ring, $R_1$ is preferably in the 2- or 3- position of the ring. When B and D together with the carbon atoms to which they are bound form an optionally substituted thiophene ring, $R_1$ is preferably in the 6- or 7- position. $R_1$ is preferably hydrogen. Each of $R_2$ and $R_3$ preferably signifies hydrogen. In one group of compounds, $R_2$ and $R_3$ together signify oxygen.

When $R_4$ is alkyl or alkoxy, this is preferably alkyl of 1 or 2 carbon atoms or alkoxy of 1 or 2 carbon atoms, especially methyl or methoxy. When $R_4$ is halogen, this is preferably chlorine. In another preferred group of compounds, $R_4$ is hydrogen.

In one group of compounds, B and D together with the carbon atoms to which they are bound form a benzene ring. In a preferred group of compounds, B and D together with the carbon atoms to which they are bound from an optionally substituted thiophene ring. When the thiophene ring is substituted with halogen, this is preferably chlorine. When the thiophene ring is substituted with alkyl, this is preferably alkyl of 1 or 2 carbon atoms, especially methyl. The thiophene ring is preferably unsubstituted.

When B and D together with the carbon atoms to which they are bound form a benzene ring, A can be oxygen or sulphur. A can also be —CH$_2$—O— or —CH$_2$—S— in either orientation. A can also be >CR$_5$R$_6$, wherein each of $R_5$ and $R_6$, which may be the same or different, is alkyl of 1 to 4 carbon atoms, preferably 1 or 2 carbon atoms, especially methyl.

When B and D together with the carbon atoms to which they are bound form a thiophene ring, A is a group

wherein each of $R_7$ and $R_8$, which may be the same or different, is alkyl of 1 to 4 carbon atoms, preferably of 1 or 2 carbon atoms, especially methyl. $R_7$ and $R_8$ may each signify hydrogen. E and F may each signify hydrogen. E and F may together form a bond.

The invention further provides a process for the production of a compound of formula I, comprising reacting a compound of formula II,

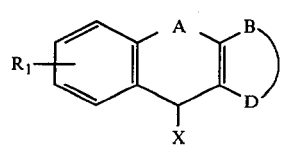

wherein A, B, D and $R_1$ are as previously defined and X is chlorine, bromine or hydroxyl, with a compound of formula III,

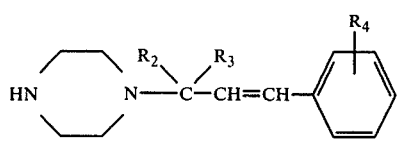

wherein $R_2$, $R_3$ and $R_4$ are as previously defined.

When A, in the compounds of formula II, is oxygen, sulphur or >CR$_5$R$_6$, X is preferably hydroxyl. When A is —CH$_2$—O—, —CH$_2$—S— or

X is preferably chlorine or bromine, especially chlorine.

The condensation of compounds of formula II with those of formula III can be effected according to known methods.

When X in the compounds of formula II is chlorine or bromine, the reaction may suitably be effected in the presence of an organic solvent which is inert under the reaction conditions, for example, a hydrocarbon or a halogenated hydrocarbon. The reaction may conveniently be effected at a temperature of from ca. 0° to 50° C., especially from ca. 0° to 20° C. The reaction may suitably be carried out in the presence of an acid binding agent, preferably an organic base or an excess of the compound of formula III.

When X in the compounds of formula II is hydroxy, the reaction may conveniently be effected in the presence of a water-removing agent, for example, p-toluene sulphonic acid, in the presence of an inert water immiscible organic solvent, for example, an aromatic hydrocarbon. The reaction may conveniently be effected at elevated temperatures, especially at the boiling temperature of the reaction mixture. The water formed may advantageously be eliminated on a water separator, and the reaction continued until the theoretical quantity of water has been formed.

The resulting compounds of formula I may be isolated and purified using conventional techniques.

Free base forms of the compounds of formula I may be converted into acid addition salt forms and vice versa in conventional manner.

The starting materials of formula II may be obtained by reducing the keto group of a compound of formula IV,

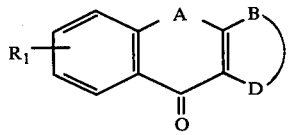

wherein $R_1$, A, B and D are as previously defined, to a hydroxy group, for example, with lithium aluminium hydride or sodium borohydride and, optionally, converting the hydroxy group to a chloro- or bromo- substituent according to known methods.

Insofar as the production of starting materials is not described, these are either known or may be produced in accordance with known processes, or in manner analogous to the processes described herein, or to known processes.

In the following non-limitative Examples, all temperatures are indicated in degress Celsius.

EXAMPLE 1

1-Cinnamyl-4-(9,10-dihydro-4H-benzo[4,5-cyclohepta[1,2-b]thiophen-4-yl)-piperazine 1.0 g of tri-n-butylbenzylammonium bromide and 47 ml of 2N caustic soda are added to a solution of 9.5 g of 1-cinnamylpiperazine in 100 ml of anhydrous chloroform and the mixture cooled to 10°. A solution of 11.0 g of 4-chloro-9,10-dihydro-4H-benzo[4,5]cyclohepta[1,2-b]thiophene in 50 ml of anhydrous chloroform is added under ice cooling and the mixture stirred at room temperature for 1.5 hours. After dilution with 300 ml of chloroform, the aqueous phase is separated off, the organic layer washed several times with water and saturated brine, dried over magnesium sulphate and evaporated. The residue is chromatographed on a column using 800 g of aluminium oxide and methylene chloride, whereby the main fraction contains the title compound (ca. 14 g).

After recrystallizing the residue once from hexane and once from ethyl acetate/petroleum ether, the title compound is obtained. M.P. 152–153°.

The 4-chloro-9,10-dihydro-4H-benzo[4,5]cyclohepta[1,2-b]thiophene employed as starting material in the above process can be obtained as follows:

10 g of 9,10-dihydro-4H-benzo[4,5]cyclohepta[1,2-b]thiophen-4-ol are dissolved in 240 ml of anhydrous benzene and saturated with dry hydrogen chloride at 10–12°. The solution is now dried twice over 10–15 g of pulverised calcium chloride, filtered and the excess hydrogen chloride driven off with nitrogen over a period of 24 hours. The benzene solution is finally evaporated to dryness at 40° and the crude residue (11.0g) used in the aforementioned process.

The following compounds of formula I can be obtained in manner analogous to that of Example 1 employing the appropriate chloride of formula II with the appropriate piperazine derivative of formula III in approximately equivalent amounts.

| Ex. No. | $R_1$ | $R_2$ | $R_3$ | $R_4$ | A |  | M.P. |
|---|---|---|---|---|---|---|---|
| 2 | H | O | | H | CH$_2$—CH$_2$ | Thiophene ring | * HCL Decomp. 125° |
| 3 | H | H | | H | H | CH$_2$—S | Benzene ring | 112–114° |
| 4 | H | O | | H | CH$_2$—S | Benzene ring | * HCL 185–187° |

* Hydrochloride salt form

EXAMPLE 5

1-Cinnamyl-4-(thioxanthen-9-yl)-piperazine

A mixture of 5.0 g of thioxanthydrol, 5.0 g of 1-cinnamylpiperazine and 1.5 ml of acetic acid in 100 ml of toluene is heated to boiling for 3 hours on a water separator. The reaction solution is decolourised with activated charcoal, evaporated to dryness and the title compound, which remains as a residue, recrystallized twice from isopropanol. M.P. 115–117°.

The following compounds of formula I can be obtained in manner analogous to that of Example 5 employing the appropriate hydroxy compound of formula II and the appropriate piperazine derivative of formula III in approximately equivalent amounts.

| Ex. No. | $R_1$ | $R_2$ | $R_3$ | $R_4$ | A | 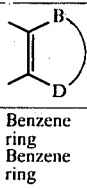 | M.P. |
|---|---|---|---|---|---|---|---|
| 6 | H | H | H | H | —O— | Benzene ring | 124–125° |
| 7 | H | H | H | H | CH₃\C/CH₃ | Benzene ring | 118–119° |

The compounds of formula I are useful because they possess pharmaceutical activity in animals. In particular, the compounds are useful as psychostimulants for stimulating the central nervous system as indicated in standard tests. For example, in one standard test, the compounds are administered p.o. to mice. The increase in excitability in the mice is then observed over a period of e.g. 2 hours. In general, the compounds are administered at a dosage of from about 10 mg to about 100 mg/kg animal body weight.

The compounds are additionally useful as vigilance-increasing agents, useful in the treatment of, for example, cerebral insufficiency, as indicated in standard tests. For example, in one test, the sleep-wakefulness cycle is determined in rats in conventional manner using an electroencephalograph. In general, the compounds are administered at a dosage of from about 10 mg to about 100 mg/kg animal body weight.

For the abovementioned uses, the dosage will, of course, vary depending on the compound employed, mode of administration and therapy desired. However, in general, satisfactory results are obtained when administered at a daily dosage of from about 0.1 mg to about 100 mg/kg animal body weight, conveniently given in divided doses 2 to 4 times a day or in sustained release form. For the larger mammal, the total daily dosage is in the range of from about 10 to about 100 mg, and dosage forms suitable for oral administration comprise from about 2.5 mg to about 50 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutically acceptable diluent or carrier. Such compositions may be formulated in conventional manner and may be, for example, a solution or a capsule.

Suitable acids for salt formation include hydrochloric, sulphuric, fumaric, maleic, malonic and naphthalene-1,5-disulphonic acids.

In one group of compounds, $R_1$ is hydrogen halogen of atomic number from 9 to 35 or alkyl of 1 to 4 carbon atoms, B is sulphur and B and D together with the carbon atoms to which they are bound form a thiophene ring which may be substituted in the position α- to the sulphur atom with halogen of atomic number from 9 to 35 or alkyl of 1 to 4 carbon atoms, $R_2$ and $R_3$ are as previously defined, $R_4$ is hydrogen, halogen of atomic number from 9 to 35, alkyl of 1 to 4 carbon atoms or alkoxy of 1 to 4 carbon atoms and A is ethylene or vinylene.

In a second group of compounds, $R_1$, $R_2$, $R_3$ and $R_4$ are as previously defined, B and D together with the carbon atoms to which they are bound form a benzene ring and A is oxygenk or sulphur.

In a third group of compounds, $R_1$, $R_2$, $R_3$ and $R_4$ are as previously defined, B and D together with the carbon atoms to which they are bound form a benzene ring and A is —CH₂—O— or —CH₂—S—.

In a fourth group of compounds, $R_1$, $R_2$, $R_3$ and $R_4$ are as previously defined, B and D together with the carbon atoms to which they are bound form a benzene ring and A is >CR₅R₆ wherein $R_5$ and $R_6$ are as previously defined.

What is claimed is:

1. A compound of formula I,

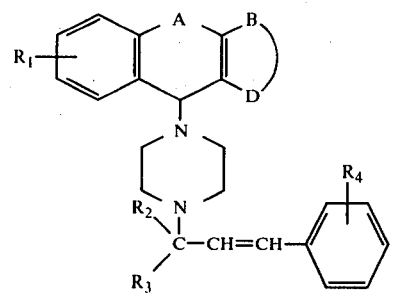

wherein each of $R_1$ and $R_4$, which may be the same or different, is hydrogen, halogen of atomic number from 9 to 35, alkyl of 1 to 4 carbon atoms or alkoxy of 1 to 4 carbon atoms, either each of $R_2$ and $R_3$ is hydrogen or $R_2$ and $R_3$ together are oxygen, either B and D together with the carbon atoms to which they are bound form a benzene ring, or B is sulphur and B and D together with the carbon atoms to which they are bound form a thiophene ring which may be substituted in the position α- to the sulphur atom with halogen of atomic number from 9 to 35 or alkyl of 1 to 4 carbon atoms, and when B and D together with the caron atoms to which they are bound form a benzene ring, A is oxygen, sulphur, —CH₂—O— or —CH₂—S— in either orientation, or when B is sulphur and B and D together with the carbon atoms to which they are bound form a substituted or unsubstituted thiophene ring, A is a group of formula

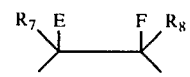

wherein each of $R_7$ and $R_8$, which may be the same or different, is hydrogen or alkyl of 1 to 4 carbon atoms and either each of E and F is hydrogen or E and F together form a bond, or a pharmaceutically acceptable acid addition salt thereof.

2. A method of increasing vigilance in animals, which comprises administering to an animal in need of such treatment a therapeutically effective amount of a compound of claim 1.

3. A method of stimulating the central nervous system in animals, which comprises administering to an animal in need of such treatment a therapeutically effective amount of a compound of claim 1.

4. A pharmaceutical composition comprising a compound of claim 1, in association with a pharmaceutically acceptable diluent or carrier.

5. A compound of claim 1, which is 1-cinnamyl-4-(9,10-dihydro-4H-benzo[4,5]cyclohepta[1,2-b]thiophen-4-yl)-piperazine.

6. A compound of claim 1, wherein $R_1$, $R_2$, $R_3$ and $R_4$ are as previously defined, B and D together with the carbon atoms to which they are bound form a benzene ring and A is oxygen or sulphur.

7. A compound of claim 1, wherein $R_1$, $R_2$, $R_3$ and $R_4$ are as previously defined, B and D together with the carbon atoms to which they are bound form a benzene ring and A is —$CH_2$—O— or —$CH_2$—S—.

8. A compound of claim 1, wherein B is sulphur and B and D together with the carbon atoms to which they are bound form a substituted or unsubstituted thiophene ring, A is a group of formula

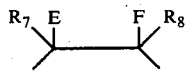

wherein each of $R_7$ and $R_8$, which may be the same or different, is hydrogen or alkyl of 1 to 4 carbon atoms and either each of E and F is hydrogen or E and F together form a bond.

9. A compound of claim 1, wherein $R_2$ and $R_3$ together are oxygen.

10. The compound according to claim 8 in which $R_1$ is hydrogen, $R_2$ and $R_3$ together is oxygen, $R_4$ is hydrogen and A is —$CH_2$—$CH_2$—.

11. The compound according to claim 7 in which $R_1$, $R_2$, $R_3$, $R_4$, and A are H, H, H, H and —$CH_2$—S—, respectively.

12. The compound according to claim 7 in which $R_1$ is hydrogen, $R_2$ and $R_3$ together is oxygen, $R_4$ is hydrogen and A is —$CH_2$—S—.

13. The compound according to claim 6 which is 1-cinnamyl-4-(thioxanthen-9-yl)-piperazine.

14. The compound according to claim 6 in which $R_1$, $R_2$, $R_3$, $R_4$ and A are H, H, H, H and —O—, respectively.

* * * * *

UNITED STATES PATENT AND TRADEMARK OFFICE
CERTIFICATE OF CORRECTION

PATENT NO. : 4,144,337
DATED : March 13, 1979
INVENTOR(S) : Jean-Michel Bastian

It is certified that error appears in the above—identified patent and that said Letters Patent are hereby corrected as shown below:

Claim 1, line 49, change "caron" to --carbon--.

Claim 4, line 10 after "comprising", insert --a therapeutically effective amount of--.

Signed and Sealed this

Fifth Day of February 1980

[SEAL]

Attest:

SIDNEY A. DIAMOND

Attesting Officer

Commissioner of Patents and Trademarks